(12) United States Patent
Carter et al.

(10) Patent No.: US 8,864,842 B2
(45) Date of Patent: Oct. 21, 2014

(54) SELF-CLEANING STENT

(75) Inventors: Matthew P. Carter, Dobson, NC (US);
Brian K. Jones, Spartanburg, SC (US)

(73) Assignee: Cook Medical Technologies LLC, Bloomington, IN (US)

( * ) Notice: Subject to any disclaimer, the term of this patent is extended or adjusted under 35 U.S.C. 154(b) by 520 days.

(21) Appl. No.: 11/820,094

(22) Filed: Jun. 18, 2007

(65) Prior Publication Data
US 2007/0299506 A1 Dec. 27, 2007

Related U.S. Application Data

(60) Provisional application No. 60/815,646, filed on Jun. 22, 2006.

(51) Int. Cl.
*A61F 2/04* (2013.01)
*A61F 2/06* (2013.01)
*A61F 2/82* (2013.01)
*A61B 17/32* (2006.01)
*A61B 17/22* (2006.01)

(52) U.S. Cl.
CPC ....... *A61F 2/82* (2013.01); *A61B 2017/320012* (2013.01); *A61B 17/22* (2013.01); *A61B 2017/320004* (2013.01)
USPC ......................................... 623/23.7; 623/1.24

(58) Field of Classification Search
USPC ................... 623/1.15, 23.64–23.7; 604/8–10, 604/890.1–892.1, 5.01–6.09
See application file for complete search history.

(56) References Cited

U.S. PATENT DOCUMENTS

| | | | | |
|---|---|---|---|---|
| 1,889,705 A | * | 11/1932 | Sherwood | 73/861.57 |
| 3,526,906 A | * | 9/1970 | De Laszlo | 623/2.27 |
| 4,479,796 A | * | 10/1984 | Kallok | 604/93.01 |
| 4,699,611 A | * | 10/1987 | Bowden | 606/191 |
| 5,004,454 A | | 4/1991 | Beyar et al. | |
| 5,217,493 A | | 6/1993 | Raad et al. | |
| 5,240,601 A | * | 8/1993 | Mazid | 210/198.2 |
| 5,291,182 A | * | 3/1994 | Wiseman | 340/610 |
| 5,380,299 A | | 1/1995 | Fearnot et al. | |
| 5,397,351 A | * | 3/1995 | Pavcnik et al. | 623/2.35 |

(Continued)

FOREIGN PATENT DOCUMENTS

| | | |
|---|---|---|
| WO | WO 99/30641 | 6/1999 |
| WO | WO 02/36047 A1 | 5/2002 |
| WO | WO 2005/072169 A2 | 8/2005 |
| WO | WO 2007/127419 A2 | 11/2007 |

OTHER PUBLICATIONS

ADI. Visual Only Indicators. Downloaded from <http://airflowdirection.com/visualonly4.htm> and <http://www.airflowdirection.com/visualonly3.htm> using WayBack Machine on <www.archive.org> for publication date of Jun. 24, 2003.*

(Continued)

*Primary Examiner* — Andrew Iwamaye
(74) *Attorney, Agent, or Firm* — Brinks Gilson & Lione

(57) ABSTRACT

A stent is provided that is able to resist clogging from cumulative matter found within a fluid that passes therethrough. The stent includes a mass moveably disposed therein, wherein movement of the stent tends to dislodge any cumulative matter accumulated within the stent. As a result, the device is able to remain resident within the patient for an extended period of time before becoming clogged and needing to be replaced.

10 Claims, 4 Drawing Sheets

(56) References Cited

U.S. PATENT DOCUMENTS

| | | | |
|---|---|---|---|
| 5,410,298 A * | 4/1995 | Wiseman | 340/610 |
| 5,647,843 A | 7/1997 | Mesrobian et al. | |
| 5,661,461 A * | 8/1997 | Wiseman | 340/610 |
| 5,782,792 A * | 7/1998 | Jones et al. | 604/6.05 |
| 5,798,697 A * | 8/1998 | Wiseman | 340/610 |
| 5,993,483 A * | 11/1999 | Gianotti | 623/1.22 |
| 6,066,088 A * | 5/2000 | Davis | 600/29 |
| 6,165,209 A * | 12/2000 | Patterson et al. | 623/1.1 |
| 6,302,917 B1 | 10/2001 | Dua et al. | |
| 6,416,540 B1 * | 7/2002 | Mathur | 623/1.15 |
| 6,419,657 B1 * | 7/2002 | Pacetti | 604/99.04 |
| 6,530,951 B1 | 3/2003 | Bates et al. | |
| 6,740,077 B1 * | 5/2004 | Brandau et al. | 604/892.1 |
| 6,746,489 B2 | 6/2004 | Dua et al. | |
| 6,774,278 B1 | 8/2004 | Ragheb et al. | |
| 6,918,927 B2 | 7/2005 | Bates et al. | |
| 7,550,005 B2 | 6/2009 | Bates et al. | |
| 7,611,533 B2 | 11/2009 | Bates et al. | |
| 2002/0045157 A1 * | 4/2002 | Hirai et al. | 435/2 |
| 2002/0058032 A1 * | 5/2002 | Hirai et al. | 424/140.1 |
| 2002/0098278 A1 * | 7/2002 | Bates et al. | 427/2.1 |
| 2002/0111620 A1 * | 8/2002 | Cooper et al. | 606/41 |
| 2003/0028243 A1 | 2/2003 | Bates et al. | |
| 2003/0036794 A1 | 2/2003 | Ragheb et al. | |
| 2003/0069552 A1 * | 4/2003 | O'Keefe et al. | 604/278 |
| 2004/0068241 A1 | 4/2004 | Fischer, Jr. | |
| 2004/0073284 A1 | 4/2004 | Bates et al. | |
| 2004/0249441 A1 * | 12/2004 | Miller et al. | 623/1.15 |
| 2005/0008763 A1 | 1/2005 | Schachter | |
| 2005/0060044 A1 * | 3/2005 | Roschak et al. | 623/23.65 |
| 2005/0125072 A1 * | 6/2005 | Kolb | 623/23.7 |
| 2006/0089589 A1 * | 4/2006 | Portnoy | 604/9 |
| 2008/0269546 A1 | 10/2008 | Wilkie et al. | |

OTHER PUBLICATIONS

International Search Report for International Application No. PCT/US2007/014214, dated Dec. 7, 2007, 4 pages.

Written Opinion of the International Searching Authority for International Application No. PCT/US2007/014214, dated Dec. 7, 2007, 6 pages.

PCT Notification of Transmittal of the International Preliminary Report on Patentability from PCT International Application No. PCT/US2007/014214 dated Sep. 10, 2008 (11 pages).

European Patent Office Communication dated Jun. 8, 2010, 4 pages.

Canadian Intellectual Property Office Action dated Jul. 30, 2010, 3 pages.

International Search Report dated Jun. 1, 2010, issued in related International Patent Application No. PCT/US2010/029561.

Response to the Canadian Intellectual Property Office Examiner's Report dated Jul. 30, 2010 (13 pages).

Canadian Intellectual Property Office Examiner's Report dated Jan. 31, 2011 (4 pages).

International Preliminary Report on Patentability dated Mar. 3, 2011, issued in related International Patent Application No. PCT/US2010/029561 (11 pages).

European Patent Office Communication dated Feb. 7, 2011 from EPO Application No. 07 809 644.3-2320, (26 pages).

Jul. 6, 2011 Response to the Canadian Patent Office Examiner's Report dated Jan. 31, 2011 for Canadian Application No. 2,659,735, (5 pages).

* cited by examiner

US 8,864,842 B2

SELF-CLEANING STENT

RELATED APPLICATIONS

The present patent document claims the benefit of the filing date under 35 U.S.C. §119(e) of Provisional U.S. Patent Application Ser. No. 60/815,646, filed Jun. 22, 2006, which is hereby incorporated by reference in its entirety.

FIELD OF THE INVENTION

The present invention relates to implantable medical devices. More particularly, the invention relates to stents, including stents adapted for use in the biliary tract.

BACKGROUND OF THE INVENTION

Stents are frequently used to enlarge, dilate, or maintain the patency of narrowed body lumens. Non-expandable stents are typically made from plastics and contain a lumen extending throughout.

Implantation of biliary stent structures provides treatment for various conditions, such as obstructive jaundice. Biliary stenting treatment approaches can be used to provide short-term treatment of conditions such as biliary fistulae or giant common duct stones. Biliary stents may be implanted to treat chronic conditions such as postoperative biliary stricture, primary sclerosing cholangitis and chronic pancreatitis.

A biliary stent can be made in the form of a polymer tube that can be advanced on a delivery catheter through an endoscope and into the bile duct where it is deployed. The tubular stent is selected to be sufficiently strong to resist collapse to maintain an open lumen through which digestive liquids can flow into the digestive tract. Among the desirable features of such a stent is that it be longitudinally flexible to be advanced along a path that may include sharp bends. The stent also should maintain its intended position within the bile duct without migrating from that position.

As bodily fluid travels through the lumen of the stent, cumulative matter within the bodily fluid adheres to the inner surface of the stent. Cumulative matter is material traversing the stent that if undisturbed, would otherwise accumulate on the passageway surfaces to reduce the diameter of the flow path and could eventually clog the stent. Cumulative matter includes, but is not limited to biofilm, bacterial growth, and sludge deposition. Thus, cumulative matter can prevent further bodily fluid from passing therethrough. A biliary stent can become occluded within a bile duct, as cumulative material, such as an encrustation of amorphous biological material and bacteria ("sludge"), accumulates on the surface of the stent gradually obstructing the lumen of the stent. Biliary sludge is an amorphous substance often containing crystals of calcium bilirubinate and calcium palimitate, along with significant quantities of various proteins and bacteria. Sludge can deposit rapidly upon implantation in the presence of bacteria. For example, bacteria can adhere to plastic stent surfaces through pili or through production of a mucopolysaccharide coating. Bacterial adhesion to the surface of a stent lumen surface can lead to occlusion of the stent lumen as the bacteria multiply within a glycocalyx matrix of the sludge to form a biofilm over the sludge within the lumen of an implanted drainage stent. The biofilm can provide a physical barrier protecting encased bacteria from antibiotics. With time, an implanted biliary stent lumen can become blocked, thereby restricting or blocking bile flow through the biliary stent. As a result, a patient can develop symptoms of recurrent biliary obstruction due to restricted or blocked bile flow through an implanted biliary stent, which can be complicated by cholangitis and sepsis.

Often, such conditions are treated by antibiotics and/or endoscopic replacement of an obstructed biliary stent. Typically, biliary stents need replacing every three months. Replacement procedures cause medical risk and financial strain to the patient.

There exists a need in the art for an implantable medical device that prevents or reduces the biofilm and sludge deposition process inside the lumen of implantable drainage stents, such as biliary stents. There is a need for a non-expandable stent that resists clogging, for example by mechanical means.

BRIEF SUMMARY OF THE INVENTION

In a first aspect of the present invention, a self-cleaning stent is provided. The device includes an elongated tubular body having a first portion, a second portion, and a lumen extending throughout. The device also includes a weighted object that is movably disposed about the elongated tubular body. The weighted object is configured to dislodge cumulative matter disposed within the elongated tubular body. The device further includes a securing mechanism configured for securing the weighted object about the elongated tubular body.

In a second aspect of the present invention, a self-cleaning stent is provided. The device includes an elongated tubular body having a first portion, a second portion, a lumen extending throughout, and at least one side drainage port. The device further includes at least one weighted object moveably disposed within the elongated tubular body, wherein the weighted object is configured to dislodge cumulative matter disposed within the elongated tubular body. The device further includes a securing mechanism for maintaining the weighted object within the elongated tubular body.

In a third aspect of the present invention, a method for preventing occlusion of a stent is provided. The method includes providing a self-cleaning stent having an elongated tubular body and at least one weighted object moveably disposed about the elongated tubular body. The weighted object is configured to dislodge cumulative matter disposed within the elongated tubular body in response to a force selected from the group consisting of patient movement, fluid flow, and changes in the gravitational force. The method further includes implanting the self-cleaning stent into a bodily lumen of a patient.

In addition, a self-cleaning stent is provided. The device includes an elongated tubular body having a first portion, a second portion, and a lumen extending throughout, a weighted object that is movably disposed about the elongated tubular body, wherein the weighted object is configured to at least partially dislodge cumulative matter deposited within the elongated tubular body to facilitate maintenance of a flow path therethrough, and a securing mechanism configured for securing the weighted object about the elongated tubular body.

In addition, a self-cleaning stent is provided. The device includes an elongated tubular body having a first portion, a second portion, a lumen extending throughout, and at least one side drainage port, at least one weighted object moveably disposed within the elongated tubular body, wherein the weighted object is configured to at least partially dislodge cumulative matter deposited within the elongated tubular body to facilitate maintenance of a flow path therethrough, and a securing mechanism for maintaining the weighted object within the elongated tubular body.

In addition, a method for preventing occlusion of a stent is provided. The method includes providing a self-cleaning stent having an elongated tubular body and at least one weighted object moveably disposed about the elongated tubular body, wherein the weighted object is configured to at least partially dislodge cumulative matter deposited within the elongated tubular body to facilitate maintenance of a flow path therethrough in response to a force selected from the group consisting of patient movement, fluid flow, and changes in the gravitational force and implanting the self-cleaning stent into a bodily lumen of a patient.

BRIEF DESCRIPTION OF THE SEVERAL VIEWS OF THE DRAWINGS

The embodiments will be further described in connection with the attached drawing figures. It is intended that the drawings included as a part of this specification be illustrative of the embodiments and should in no way be considered as a limitation on the scope of the invention.

DETAILED DESCRIPTION OF PRESENTLY PREFERRED EMBODIMENTS

Figure 1:
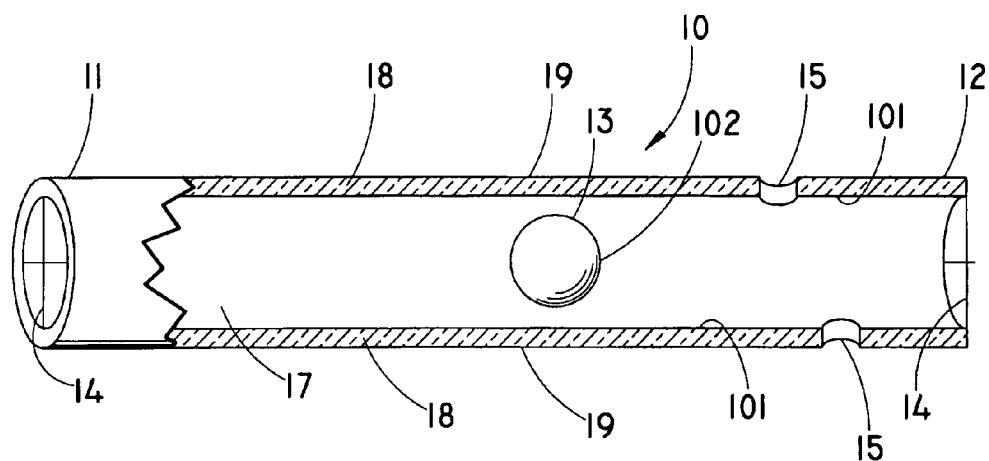
FIG. 1 is a partial cross sectional perspective view of a self-cleaning stent.
Figure 2:
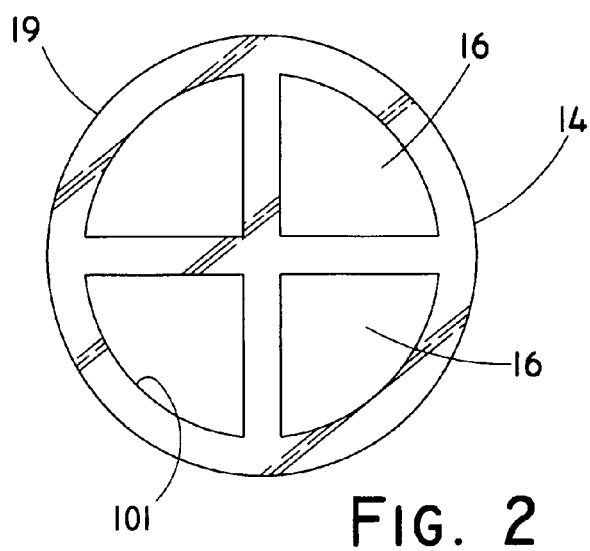
FIG. 2 is an end view of the self-cleaning stent depicted in FIG. 1.

The exemplary embodiments disclosed herein provide self-cleaning stents that are able to at least inhibit long term adherence of cumulative matter to the interior of the stent so that the amount of time the stent can reside within a patient before needing to be replaced is extended. The present invention is not limited to non-expandable stents; it is contemplated that self-expanding stents can also be improved by the inventive concepts disclosed herein. Furthermore, the present invention is not limited to use within any particular part of the body or for use with humans.

A more detailed description of the embodiments will now be given with reference to FIGS. 1-8. Throughout the disclosure, like reference numerals and letters refer to like elements. The present invention is not limited to the embodiments illustrated; to the contrary, the present invention specifically contemplates other embodiments not illustrated but intended to be included in the claims.

FIG. 1 is a partial cross sectional perspective view of an illustrative embodiment of a self-cleaning biliary stent. Self-cleaning stent 10 comprises a first portion 11, second portion 12, and a lumen 17 extending throughout. Walls 18 of self-cleaning stent 10 are about 0.020 inches thick and the outer diameter of self-cleaning stent 10 is about 3-10 French. However, other sizes are contemplated depending on the needs of the patient, the size of weighted object 13, and the diameter of the body lumen in which self-cleaning stent 10 will dwell. Side drainage ports 15 contained within walls 18 allow for additional fluid to pass therethrough. Side drainage ports 15 can be configured in such a way that side drainage ports 15 do not come in contact with tissue; e.g. side drainage ports 15 can be placed near second portion 12 or first portion 11 of walls 18, wherein such portion of walls 18 would not come in contact with any portion of the bodily tissue wherein self-cleaning stent 10 dwells. For example, second portion 12 configured with side drainage ports 15 can be extended out into the duodenum such that side drainage ports 15 do not contact and therefore, are not blocked by, any tissue.

Contained within self-cleaning stent 10 is weighted object 13 that is free to move about lumen 17. Weighted object 13 is made from ceramic, stainless steel, or gold. However, other medically acceptable materials are also contemplated, including but not limited to, materials that are very inert and have a high density. Weighted object 13 moves longitudinally within lumen 17 in response to patient movement, fluid flow, and/or changes in the gravitational force. As weighted object 13 moves, it contacts inner surface 101 of walls 18 so as to dislodge any cumulative matter attached thereto. The cumulative matter then exits through first portion 11 or second portion 12 of self-cleaning stent 10. Cumulative matter can also exit via side drainage ports 15. Weighted object 13 is preferably 5-10 grams; however, other masses are contemplated. Weighted object 13 should be sufficiently sized and shaped such that it does not completely obstruct fluid flow and such that it is able to move about lumen 17 without causing stent 10 to become dislodged from its dwelling place. The shape of weighted object 13 is not limited to having a circular-shape; other shapes are contemplated including, but not limited to, those having a square-shape, rectangular-shape, cylindrical-shape, or triangular-shape. Additionally, weighted object 13 may have additional materials or coatings attached thereto to aid in the removal of cumulative matter.

Self-cleaning stent 10 also comprises two end cap securing mechanisms 14 (also shown in FIG. 2) that are extruded as part of walls 18, although it is contemplated that end caps 14 could be separate pieces fixedly attached to first portion 11 and second portion 12 of self-cleaning stent 10. Additionally, it is contemplated that end caps 14 could reside within walls 18 of self-cleaning stent 10. End caps 14 prevent the escape of weighted object 13 from lumen 17 and have openings 16 to allow fluid to pass therethrough. End cap 14 is not limited to having a cross-shape, but may include other configurations that are able to prevent the escape of weighted object 13 from lumen 17 and allow fluid to pass therethrough.

Walls 18 can be formed from any suitable biocompatible and biostable material. Walls 18 are preferably resiliently compliant enough to readily conform to the curvature of the duct in which it is to be placed, while having sufficient "hoop" strength to retain its form within the duct. Walls 18 of self-cleaning stent 10 are preferably made from a medium density biocompatible polyethylene, although other materials are contemplated, including but not limited to polyurethane, polytetrafluoroethylene (PTFE), stainless steel, and Nitinol. In one aspect, walls 18 are formed from a polyolefin such as a metallocene catalyzed polyethylene, polypropylene, polybutylene or copolymers thereof. Other suitable materials for walls 18 include polyurethane (such as a material commercially available from Dow Corning under the tradename PELLETHANE); a silicone rubber (such as a material commercially available from Dow Corning under the tradename SILASTIC); a polyetheretherketone (such as a material commercially available from Victrex under the tradename PEEK); vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); polyesters such as polyethyleneterephthalate (PET); polyester-ethers; polyamides such as nylon 6 and nylon 6,6; polyamide ethers; polyethers; elastomers such as elastomeric polyurethanes and polyurethane copolymers; silicones; polycarbonates; and mixtures and block or random copolymers of any of the foregoing.

The surface of self-cleaning stent 10 can be coated with a polymer. Walls 18 are illustrated as having a polymer coating on both its outer surface 19 and its inner surface 101. Weighted object 13 is illustrated as having a polymer coating on its outer surface 102. The polymer coating on outer surface 19, 102 and inner surface 101 can be a biocompatible polymer, including but not limited to PTFE. Polymer coating can also comprise a hydrophilic polymer selected from the group comprising polyacrylate, copolymers comprising acrylic acid, polymethacrylate, polyacrylamide, poly(vinyl alcohol), poly(ethylene oxide), poly(ethylene imine), carboxymethylcellulose, methylcellulose, poly(acrylamide sulphonic acid), polyacrylonitrile, poly(vinyl pyrrolidone), agar, dextran, dextrin, carrageenan, xanthan, and guar. The hydrophilic polymers can also include ionizable groups such as acid groups, e.g., carboxylic, sulphonic or nitric groups. The hydrophilic polymers may be cross-linked through a suitable cross-binding compound. The cross-binder actually-used depends on the polymer system: if the polymer system is polymerized as a free radical polymerization, a preferred cross-binder comprises two or three unsaturated double bonds.

The polymer coating on inner surface 101 and outer surface 19, 102 can also be loaded with a variety of bioactive agents. The bioactive agent preferably includes one or more antimicrobial agents. The term "antimicrobial agent" refers to a bioactive agent effective in the inhibition of, prevention of or protection against microorganisms such as bacteria, microbes, fungi, viruses, spores, yeasts, molds and others generally associated with infections such as those contracted from the use of the medical articles described herein. The antimicrobial agents include antibiotic agents and antifungal agents.

Antibiotic agents may include cephalosporins, clindamycin, chloramphenicol, carbapenems, penicillins, monobactams, quinolones, tetracycline, macrolides, sulfa antibiotics, trimethoprim, fusidic acid and aminoglycosides. Antifungal agents may include amphotericin B, azoles, flucytosine, cilofungin and nikkomycin Z. Specific non-limiting examples of suitable antibiotic agents include: ciprofloxacin, doxycycline, amoxicillin, metronidazole, norfloxacin (optionally in combination with ursodeoxycholic acid), ciftazidime, and cefoxitin. Other suitable antibiotic agents include rifampin, minocycline, novobiocin and combinations thereof discussed in U.S. Pat. No. 5,217,493 (Raad et al.), which is incorporated herein by reference in its entirety. Rifampin is a semisynthetic derivative of rifamycin B, a macrocyclic antibiotic compound produced by the mold *Streptomyces mediterranic*. Rifampin is believed to inhibit bacterial DNA-dependent RNA polymerase activity and is bactericidal in nature. Rifampin is available in the United States from Merrill Dow Pharmaceuticals, Cincinnati, Ohio. Minocycline is a semisynthetic antibiotic derived from tetracycline. It is primarily bacteriostatic and is believed to exert an antimicrobial effect by inhibiting protein synthesis. Minocycline is commercially available as the hydrochloride salt which occurs as a yellow, crystalline powder and is soluble in water and slightly soluble in alcohol. Minocycline is available from Lederle Laboratories Division, American Cyanamid Company, Pearl River, N.Y. Novobiocin is an antibiotic obtained from cultures of *Streptomyces niveus* or *S. spheroides*. Novobiocin is usually bacteriostatic in action and is believed to interfere with bacterial cell wall synthesis and inhibit bacterial protein and nucleic acid synthesis. Novobiocin also appears to affect stability of the cell membrane by complexing with magnesium. Novobiocin is available from The Upjohn Company, Kalamazoo, Mich.

The polymer coating is preferably capable of releasing the bioactive agent into the body at a predetermined time and at a predetermined rate. Such polymeric coatings include drug-eluting matrix materials described in U.S. Pat. Nos. 5,380, 299, 6,530,951, 6,774,278 and U.S. patent application Ser. Nos. 10/218,305, 10/223,415, 10/410,587, 10/000,659, and 10/618,977 all of which are incorporated in their entirety herein by reference.

Alternatively, different polymer coatings can be coated on outer surface 19, 102 and inner surface 101. For example, the polymer coating on outer surface 19 can include any polymer coating commonly known to those skilled in the art to help reduce tissue irritation incurred as a result of self-cleaning stent 10 being in contact with a passageway of the patient for a prolonged period of time. The polymer coating on inner surface 101 and outer surface 102 can also include any coating commonly known to those skilled in the art to further help prevent clogging of self-cleaning stent 10.

Alternatively, inner surface 101 and outer surface 19, 102 of self-cleaning stent 10 can be composed from a biodegradable polymer that gradually bioerodes with time. Biodegradable polymers may include rigid dissolvable polymers such as poly(lactid acid), poly(glycolic acid), and poly-epsilon-capro-lactone, or combinations thereof. Other rigid dissolvable polymers will be apparent to those of ordinary skill in the art. Suitable biodegradable polymers may be selected from the group consisting of: a hydrogel, an elastin-like peptide, a polyhydroxyalkanoates (PHA), polyhydroxybutyrate compounds, and co-polymers and mixtures thereof. The biodegradable material can be selected and varied based on various design criteria. The biodegradable material preferably comprises one or more hydrolyzable chemical bonds, such as an ester, a desired degree of crosslinking, a degradation mechanism with minimal heterogeneous degradation, and nontoxic monomers. The biodegradable material is preferably a polyhydroxyalkanoate compound, a hydrogel, poly(glycerol-sebacate) or an elastin-like peptide. Desirably, the biodegradable material comprises a poly-α-hydroxy acid, such as polylactic acid (PLA). PLA can be a mixture of enantiomers typically referred to as poly-D,L-lactic acid. Alternatively, the biodegradable material is poly-L-(+)-lactic acid (PLLA) or poly-D(−)-lactic acid (PDLA), which differ from each other in their rate of biodegradation. PLLA is semicrystalline. In contrast, PDLA is amorphous, which can promote the homogeneous dispersion of an active species. Unless otherwise specified, recitation of "PLA" herein refers to a biodegradable polymer selected from the group consisting of: PLA, PLLA and PDLA.

Self-cleaning stent 10 comprising a drug-releasing coating may be formed by any suitable process conventionally used to shape polymeric materials such as thermoplastic and elastomeric materials. Shaping processes can include, but not limited to, extrusion including coextrusion, molding, calendaring, casting and solvent coating. Preferred shaping processes include extrusion and coextrusion processes. For example, a biodegradable coating polymer mixed with a drug may be applied to inner surface 101 of self-cleaning stent 10 by applying a solvent solution or liquid dispersion of a biodegradable polymer onto a surface of the walls 18 followed by removing the solvent or liquid dispersing agent, e.g., by evaporation. Such a solution or dispersion of the biodegradable polymer may be applied by contacting a surface of the support member with the solution or dispersion by, for example, dipping or spraying. For example, the biodegradable coating may be applied by spraying a solution of a biodegradable polymer onto walls 18 within the lumen of self-cleaning stent 10. Alternatively, a coated self-cleaning stent 10 can be formed by applying a polymer to the exterior surface of a biodegradable coating to form a multilayer medical device. For example, a solution of a biostable polymer can be applied to the external surface of a tube of the biodegradable coating and dried in place to form self-cleaning stent 10.

Alternatively, each of the multiple layers may be solvent cast. The second layer is cast from a solvent that does not dissolve the already-cast layer. For example, a polyurethane used to form self-cleaning stent 10 may be dissolved in dimethylformamide, while PLA used to form a biodegradable coating may be dissolved in dichloromethane. Where the second solvent does not dissolve the support member polymer, the second solution may be spread on the first layer once dry, and the solvent evaporated off. The resulting multi-layers have a strong bond between the layers.

Biodeposition-reducing bioactive agents can be selected to withstand the extrusion temperature. In a first aspect, a bioactive agent may be included within, or mixed with, the polymer prior to extrusion. Extrusion of the film allows inclusion of a drug or agent that can withstand the extrusion temperatures. For example, the antimicrobial agents described in U.S. patent application US2005/0008763A1 are compatible with this manufacturing technique, which is incorporated herein by reference in its entirety. The bioactive agent preferably does not materially interfere with the physical or chemical properties of the biodegradable material in which it is included. The bioactive agent and the biodegradable material may be preformed using any of the conventional devices known in the art for such purposes. Where thermoplastic materials are employed, a polymer melt may be formed by heating the various agents, which can then be mixed to form a homogenous mixture. A common way of doing so is to apply mechanical shear to a mixture of the matrix polymer and additives. Devices in which the biodegradable material and the bioactive(s) may be mixed in this fashion include, but are not limited to, devices such as a single screw extruder, a twin screw extruder, a banbury mixer, a high-speed mixer, and a ross kettle.

In a second aspect, the biodegradable coating is adhered to self-cleaning stent 10 without a bioactive agent, and the bioactive agent may be subsequently absorbed into the biodegradable coating after the formation of the device. For example, the biodegradable coating can be contacted with a solution of the bioactive agent within the drainage lumen of self-cleaning stent 10. The effective concentration of the bioactive agent within the solution can range from about 1 to 10 μg/ml for minocycline, preferably about 2 μg/ml; 1 to 10 μg/ml for rifampin, preferably about 2 μg/ml; and 1 to 10 μg/ml for novobiocin, preferably about 2 μg/ml. The solution is preferably composed of sterile water or sterile normal saline solutions.

Figure 3:
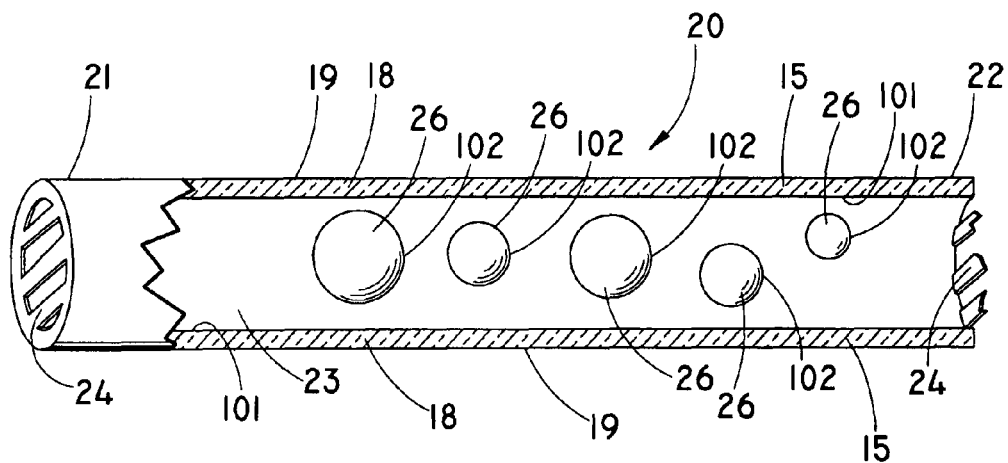
FIG. 3 is a partial cross sectional perspective view of another self-cleaning stent.
Figure 4:
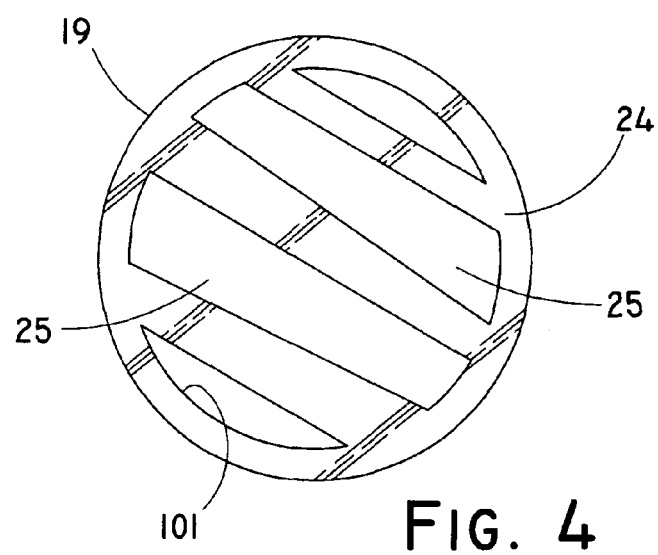
FIG. 4 is an end view of the self-cleaning stent depicted in FIG. 3.

FIG. 3 depicts an alternate illustrative embodiment of a self-cleaning stent. Self-cleaning stent 20 comprises end cap securing mechanisms 24 (also shown in FIG. 4) that are extruded as part of walls 18, although it is contemplated that end caps 24 could be separate pieces fixedly attached to first portion 21 and second portion 22 of self-cleaning stent 20. Additionally, it is contemplated that end caps 24 could reside within walls 18 of self-cleaning stent 20. End caps 24 prevent the escape of weighted objects 26 and provide openings 25 to allow fluid to pass through lumen 23. End cap 24 is not limited to having a diagonal shape, but may include other configurations that are able to prevent the escape of weighted objects 26 from lumen 23 and allow fluid to pass therethrough.

Within lumen 23 are multiple weighted objects 26 having differing sizes. Weighted objects 26 are able to move about freely within lumen 23. In response to patient movement, fluid flow, and/or changes in the gravitational force, weighted objects 26 move and come in contact with each other and with inner surface 101 of walls 18 and dislodge cumulative matter attached thereto. Although depicted as having a circular-shape, weighted objects 26 can have a variety of different shapes, including but not limited to a square-shape, rectangular-shape, cylindrical-shape, or triangular-shape. Additionally, a particular weighted object 26 may have a shape, size, and coating 102 different from that of another weighted object 26. Additionally, weighted objects 26 may have additional materials or coatings attached thereto to aid in the removal of cumulative matter.

Figure 5:
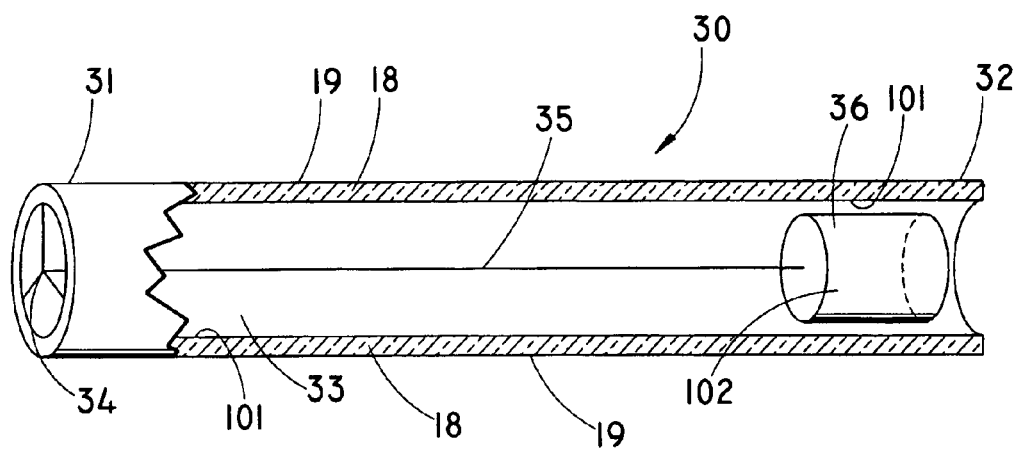
FIG. 5 is a partial cross sectional perspective view of another self-cleaning stent.

FIG. 5 depicts another illustrative embodiment of a self-cleaning biliary stent. Weighted object 36 is connected via a line 35 to first portion 31 via a connection point securing mechanism 34. Line 35 is a stainless steel braided cable. However other configurations are contemplated, including but not limited to, a plastic line and a nylon line. Line 35 limits the distance to which weighted object 36 can travel in the direction of second portion 32; therefore, second portion 32 of self-cleaning stent 30 need not be partially occluded. Additionally, line 35 can be connected to weighted object 36 such that it offsets the center of gravity of weighted object 36. Additionally, weighted object 36 can be configured in such a way that the center of gravity is not located directly at the center of weighted object 36; thus, weighted object 36 would be more likely to move about lumen 33.

Weighted object 36 moves within lumen 33 of self-cleaning stent 30 in response to patient movement, fluid flow, and/or changes in the gravitational force. As weighted object 36 moves about lumen 33, it contacts inner surface 101 of walls 18 so as to dislodge cumulative matter attached thereto. The shape of weighted object 36 is not limited to having a cylindrical shape. Other shapes are contemplated including, but not limited to, those having a square-shape, rectangular-shape, circular-shape, or triangular-shape. Additionally, weighted object 36 may have additional materials or coatings attached thereto to aid in the removal of cumulative matter.

Additionally, line 35 can be configured such that weighted object 36 extends out from stent 30 so as to act as a pendulum. As such, line 35 would scrape against inner surface 101 of walls 18 dislodging cumulative matter attached thereto. Such a configuration may be beneficial when self-cleaning stent 30 is used in the duodenum, wherein second portion 32 is configured to extend into the duodenum with weighted object 36 acting as a pendulum hanging in the duodenum.

Figure 6:
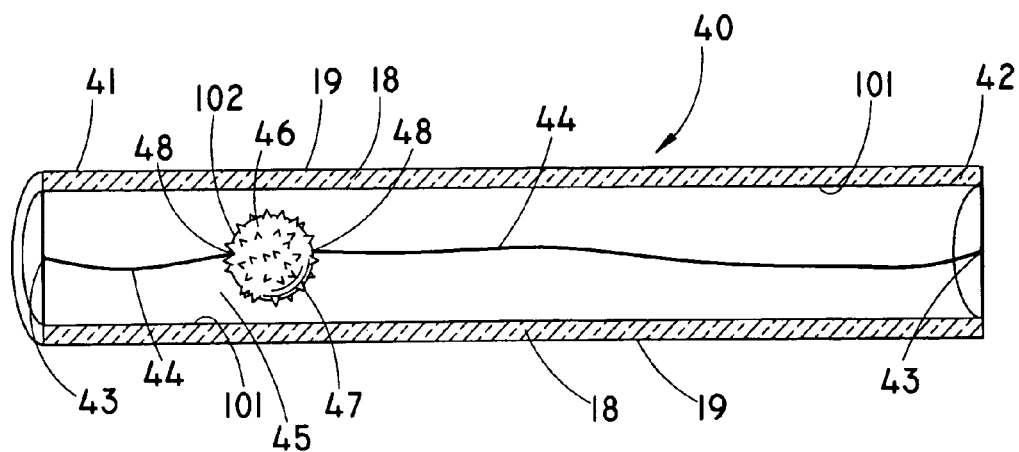
FIG. 6 is a partial cross sectional perspective view of another self-cleaning stent.

FIG. 6 depicts another illustrative embodiment of a self-cleaning stent. Connection point securing mechanisms 43 are located at first portion 41 and second portion 42 of self-cleaning stent 40. Attached to connection points 43 is a line 44 that passes through lumen 48 of weighted object 46 such that weighted object 46 freely slides along line 44. Weighted object 46 moves within lumen 45 of self-cleaning stent 40 in response to patient movement, fluid flow, and/or changes in the gravitational force. Connection points 43 restrict the movement of weighted object 46 to within lumen 45, however, line 44 has slack so that weighted object 46 is able to contact inner surface 101 of walls 18. As weighted object 46 moves about lumen 45, bristles 47 contact inner surface 101 of walls 18 so as to dislodge cumulative matter attached thereto. The shape of weighted object 46 is not limited to having a circular-shape; other shapes are contemplated including, but not limited to, those having a rectangular-shape, square-shape, cylindrical-shape, or triangular-shape. Furthermore, weighted object 46 is not limited to having triangular-shaped bristles 47, other shapes are contemplated including, but not limited to, those having a square-shape, cylindrical-shape, rectangular-shaped, or circular-shape. Additionally, it is contemplated that additional weighted objects having the same or different sizes, shapes, and coatings 102 could be added along line 44. Additionally, it is further contemplated that more than one sliding line 44 could be contained within lumen 45, wherein each line has at least one weighted object attached thereto. Additionally, weighted object 46 may have coatings 102 attached thereto to aid in the removal of cumulative matter.

Figure 7:
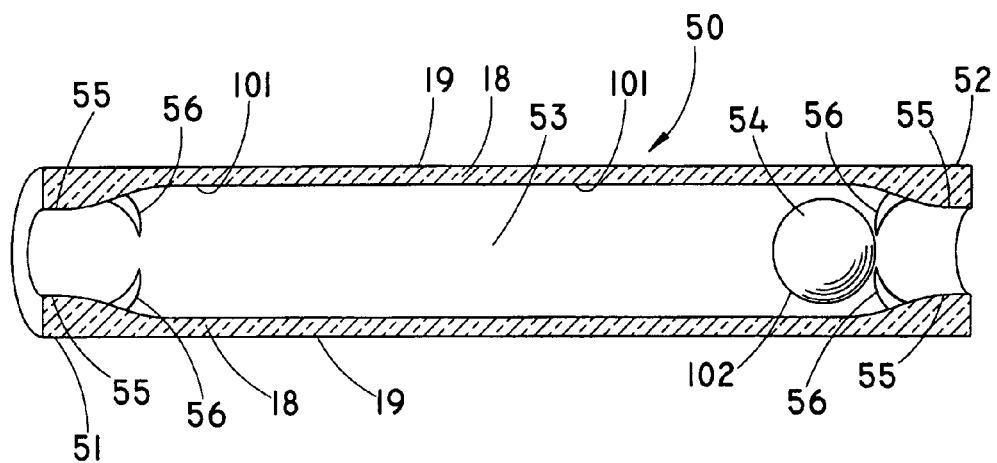
FIG. 7 is a partial cross sectional perspective view of another self-cleaning stent.

FIG. 7 depicts yet another embodiment of a self-cleaning stent. Self-cleaning stent 50 has a lumen 53 extending throughout so that fluid can pass therethrough. First portion 51 and second portion 52 of self-cleaning stent 50 have an inner diameter 55 that is less than the outer diameter of weighted object 54 to secure weighted object 54 within self-cleaning stent 50. In addition, prongs 56 prevent weighted object 54 from occluding inner diameter 55 located at first portion 51 or second portion 52. Although only one weighted object is depicted, it is contemplated that a plurality of weighted objects can be used, including those having different sizes, shapes, and coatings from that depicted in FIG. 7. Additionally, weighted object 54 may have additional materials or coatings attached thereto to aid in the removal of cumulative matter.

Figure 8:
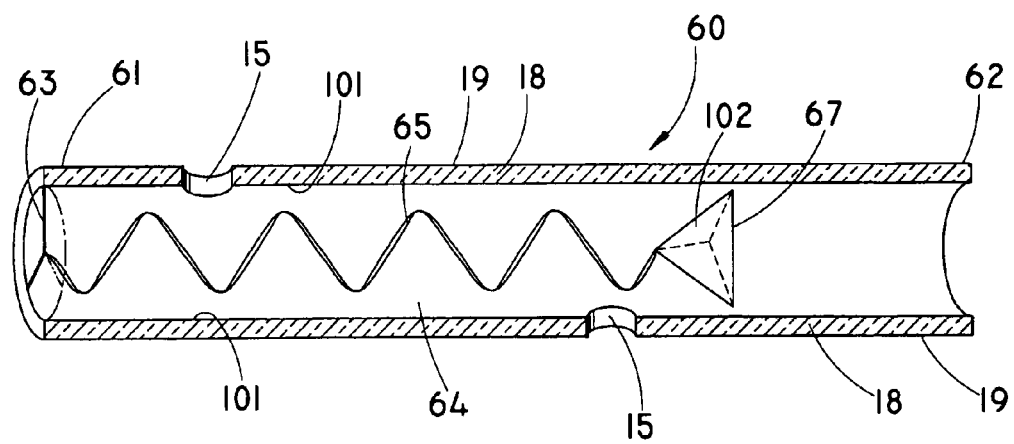
FIG. 8 is a partial cross sectional perspective view of another self-cleaning stent.

FIG. 8 depicts yet another embodiment of a self-cleaning stent having side drainage ports 15. Located at first portion 61 of self-cleaning stent 60 is a connection point securing mechanisms 63 to which a helical spring 65 is connected. Spring 65 is also connected to weighted object 67. Spring is biased in the direction of first portion 61; in response to patient movement, fluid flow, and/or changes in the gravitational force, weighted object 67 will temporarily distend spring 65 causing weighted object 67 to move longitudinally within lumen 64 in the direction of second portion 62. When the patient movement, fluid flow, and/or changes in the gravitational force are no longer present, spring 65 will retract pulling weighted object 67 in the direction of first portion 61. Preferably, the spring rate is minimized and the mass of weighted object 67 is maximized so that weighted object 67 is easily moved. As weighted object 67 moves within lumen 64, weighted object 67 contacts inner surface 101 of walls 18 dislodging cumulative matter attached thereto. Additionally, weighted object 67 may have additional materials or coatings attached thereto to aid in the removal of cumulative matter.

The foregoing description and drawings are provided for illustrative purposes only and are not intended to limit the scope of the invention described herein or with regard to the details of its construction and manner of operation. It will be evident to one skilled in the art that modifications and variations may be made without departing from the spirit and scope of the invention. Changes in form and in the proportion of parts, as well as the substitution of equivalence, are contemplated as circumstances may suggest and render expedience; although specific terms have been employed, they are intended in a generic and descriptive sense only and not for the purpose of limiting the scope of the invention set forth in the following claims.

What is claimed is:

1. A self-cleaning biliary stent comprising:
   an elongated tubular body having a first end, a second end, and a stent lumen extending throughout;
   a weighted object that is movably disposed within the stent lumen of the elongated tubular body, wherein the weighted object is uncoupled to the elongated tubular body such that it is configured to move freely in longitudinal and transverse directions in the stent lumen in response to movement of the stent when the stent is disposed inside a bile duct lumen, to at least partially dislodge cumulative matter deposited within the stent lumen to facilitate maintenance of a bile fluid flow path there through; and
   a securing mechanism configured for securing the weighted object within the stent lumen;
   wherein the elongated tubular body is continuous with an interruption for a side drainage port;
   wherein the elongated tubular body is shaped and sized to be implanted within the bile duct lumen so as to maintain a bile fluid pathway through the bile duct lumen;
   wherein the cumulative matter is selected from the group consisting of biofilm, bacteria growth, and sludge;
   wherein the securing mechanism comprises a first and a second end cap;
   wherein the first end cap is attached to the first end of the elongated tubular body and the second end cap is attached to the second end of the elongated tubular body;
   wherein the end caps each have a plurality of openings there through defined by one or more linear transverse members;
   wherein a maximum cross-sectional area of each of the plurality of openings is smaller than a maximum cross-sectional area of the weighted object so as to prevent the weighted object from passing through any of the plurality of openings and wherein the plurality of openings are configured to allow for uninterrupted flow of bile there through;
   wherein the weighted object is sized and shaped such that it does not completely obstruct a bile fluid flow through the stent lumen and the end caps so as to maintain the bile fluid flow path there through irrespective of the position of the weighted object within the stent lumen; and
   wherein the end caps are configured not to inhibit transverse movement of the weighted object.

2. The self-cleaning biliary stent of claim 1 wherein the weighted object moves about the stent lumen in response to a force selected from the group consisting of patient movement, fluid flow, and changes in the gravitational force.

3. The self-cleaning biliary stent of claim 1 wherein the weighted object comprises at least two weighted objects.

4. The self-cleaning biliary stent of claim 1 wherein bristles are disposed about a surface of the weighted object.

5. The self-cleaning biliary stent of claim 1 wherein the weighted object has a shape selected from the group consisting of a square, a rectangle, a circle, a cylinder, and a triangle.

6. The self-cleaning biliary stent of claim 1 wherein at least one of an inner surface of the elongated tubular body, an outer surface of the elongated tubular body, and the weighted object is coated with a polymer.

7. The self-cleaning biliary stent of claim 1 wherein the elongated tubular body has an outer diameter of about 3-10 French.

8. The self-cleaning biliary stent of claim 1 wherein the weighted object has a mass of about 5-10 grams.

9. The self-cleaning stent of claim 1 wherein the weighted object is made from a material selected from the group consisting of gold, ceramic, and stainless steel.

10. The self-cleaning biliary stent of claim 1 wherein the elongated tubular body has a thickness of about 0.020 inches.

* * * * *